(12) United States Patent
Kim

(10) Patent No.: US 10,011,855 B2
(45) Date of Patent: Jul. 3, 2018

(54) FRACTIONATED COUPLED APPARATUS FOR SACCHARIFYING BIOMASS AND METHOD FOR SACCHARIFYING BIOMASS USING THE SAME

(71) Applicant: SK Innovation Co., Ltd., Seoul (KR)

(72) Inventor: Tae Wan Kim, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 24 days.

(21) Appl. No.: 15/233,228

(22) Filed: Aug. 10, 2016

(65) Prior Publication Data

US 2017/0088870 A1   Mar. 30, 2017

(30) Foreign Application Priority Data

Sep. 25, 2015 (KR) .......... 10-2015-0136203
Feb. 18, 2016 (KR) .......... 10-2016-0019357

(51) Int. Cl.
*C12P 19/14* (2006.01)
*C12M 1/00* (2006.01)
*C12P 19/02* (2006.01)

(52) U.S. Cl.
CPC ............ *C12P 19/14* (2013.01); *C12M 29/00* (2013.01); *C12M 45/09* (2013.01); *C12P 19/02* (2013.01); *C12P 2201/00* (2013.01)

(58) Field of Classification Search
CPC ....................................... C12P 19/14
USPC ........................................... 435/41
See application file for complete search history.

(56) References Cited

U.S. PATENT DOCUMENTS

| | | | |
|---|---|---|---|
| 5,411,594 A | 5/1995 | Brelsford | |
| 5,733,758 A | 3/1998 | Nguyen | |
| 2013/0011327 A1 | 1/2013 | Peus et al. | |
| 2014/0060522 A1* | 3/2014 | Baynes | ............ C13K 13/007 127/30 |
| 2015/0240198 A1 | 8/2015 | Romero et al. | |

FOREIGN PATENT DOCUMENTS

| | | |
|---|---|---|
| KR | 1020130107192 A | 10/2013 |
| KR | 1020150041665 A | 4/2015 |
| WO | 2011117837 A2 | 9/2011 |
| WO | 2014039986 A1 | 3/2014 |

\* cited by examiner

*Primary Examiner* — Bin Shen
(74) *Attorney, Agent, or Firm* — The Webb Law Firm

(57) ABSTRACT

The present invention relates to a fractionated coupled apparatus for saccharifying biomass and a method for saccharifying biomass using the apparatus, and more particularly, to a fractionated coupled apparatus and method for saccharifying biomass, in which biomass mixed with enzyme is first saccharified in a single-tubular plug-flow reactor (PFR) unit, and then distributed into and saccharified in a second multi-tubular PFR unit comprising 2-100 PFRs, each having a diameter smaller than that of the single-tubular PFR unit. According to the present invention, biomass is first saccharified in a PFR having a relatively large diameter, and then distributed into and saccharified in PFRs having a relatively small diameter. Thus, a high concentration of a sugar compound can be obtained without having to use an additional mixer.

26 Claims, 2 Drawing Sheets

FRACTIONATED COUPLED APPARATUS FOR SACCHARIFYING BIOMASS AND METHOD FOR SACCHARIFYING BIOMASS USING THE SAME

CROSS-REFERENCE TO RELATED APPLICATIONS

This application claims priority to Korean Patent Application Nos. 10-2015-0136203 and 10-2016-0019357 filed Sep. 25, 2015 and Feb. 18, 2016, respectively, the disclosures of which are hereby incorporated in their entirety by reference.

TECHNICAL FIELD

The present invention relates to a fractionated coupled apparatus for saccharifying biomass and a method for saccharifying biomass using the apparatus, and more particularly, to a fractionated coupled apparatus and method for saccharifying biomass, in which biomass mixed with enzyme is first saccharified in a single-tubular plug-flow reactor (PFR) unit, and then distributed into and saccharified in a second multi-tubular PFR unit comprising 2-100 PFRs, each having a diameter smaller than that of the single-tubular PFR unit.

BACKGROUND ART

Due to environmental pollution and the shortage of petroleum resources, environmentally friendly renewable biochemical products have been of interesting interest, and studies thereon have been actively conducted. Particularly, many studies have recently been conducted to produce biochemical products, which can replace petrochemical products, from fermentable sugar based on microbial metabolic engineering. The cost-effective production of fermentable sugar, the development of microbial metabolic engineering and genetic engineering technology, and processes for the separation and purification of final products are considered the key technical factors for success in the development of such biochemical products.

In addition, if biochemical products can be produced at high concentrations, costs for separation and purification processes in subsequent stages can be reduced, thereby ensuring the price competitiveness of the final biochemical products. If cellulose-, lignocelluloses-, corn- or starch based biomass is used as a substrate at a high ratio, a high concentration of fermentable sugar can be produced. Thus, if such fermentable sugar is used as a raw material, high concentrations of biochemical products can be produced. Particularly, biochemical products are produced by fermentation processes in which a large amount of water is used, leading to an increase in the size of a reactor and an increase in energy consumption in the final isolation process, which adversely affect the price competitiveness of the final products.

U.S. Pat. No. 5,733,758 discloses a vertical tower type plug flow reactor for the saccharifying and fermenting pretreated biomass. In the invention disclosed in the above-described US patent, sugar is obtained by fermenting biomass using a multistage plug-flow reactor, but there are disadvantages in that, because mixing is performed using an additional mixer, the overall size of the system is large, and because a mixer is used to mix highly viscous sugar, a large amount of energy is used.

U.S. Pat. No. 5,411,594 discloses a two-stage plug-flow reactor for continuous saccharification of lingocellulosic biomass. In the method disclosed in the above US patent, biomass is saccharified using the two-stage plug-flow reactor, and thus the saccharification is performed with high efficiency. However, there are disadvantages in that, because two identical reactors are used, the volume of the system is large, and a large amount of energy is used to mix highly viscous sugar.

Accordingly, the present inventors have made extensive efforts to solve the above-described problems, and as a result, have found that, when a mixture of biomass and enzyme is first saccharified in a single tubular first plug-flow reactor (PFR) unit, and then distributed into and saccharified in a second multi-tubular PFR unit comprising a plurality of PFRs, each having a diameter smaller than that of the single-tubular PFR unit, a high concentration of a sugar compound can be obtained without having to use an additional mixer, and investment in a saccharification apparatus and power consumption can be reduced, thereby completing the present invention.

DISCLOSURE OF INVENTION

It is an object of the present invention to provide a fractionated coupled apparatus for saccharifying biomass and a method for saccharifying biomass using the apparatus.

To achieve the above object, the present invention provides a fractionated coupled apparatus for saccharifying biomass, comprising: (a) a first single-tubular plug-flow reactor (PFR) unit; (b) a second multi-tubular PFR unit including 2-100 PFRs, each having a diameter smaller than that of the first single-tubular PFR unit; and (c) a means for recycling a portion or all of a saccharification liquid obtained in the second multi-tubular PFR unit, to the first single-tubular PFR unit.

The present invention also provides a fractionated coupled apparatus for saccharifying biomass, comprising 2-10 plug-flow reactor (PFR) sets connected in series, wherein each of the PFR sets comprises: (a) a first single-tubular plug-flow reactor (PFR) unit; and (b) a second multi-tubular PFR unit including 2-100 PFRs, each having a diameter smaller than that of the first single-tubular PFR unit.

The present invention also provides a method of saccharifying biomass comprising the steps of: (a) mixing pretreated biomass (PTB) with a saccharifying enzyme to obtain a mixture, and passing the mixture through a first single-tubular plug-flow reactor (PFR) unit to obtain a first saccharification liquid; (b) distributing the first saccharification liquid into a second multi-tubular PFR unit to obtain a second saccharification liquid; and (c) recycling a portion or all of the second saccharification liquid of the step (b) to the first single-tubular PFR unit of the step (a).

In addition, the present invention also provides a method of saccharifying biomass comprising: (a) mixing pretreated biomass (PTB) with a saccharifying enzyme to obtain a mixture, and supplying and saccharifying the mixture into PFR sets, each comprising a first single-tubular plug-flow reactor (PFR) unit and a second multi-tubular PFR unit; (b) distributing a first saccharification liquid, produced in the first single-tubular PFR unit, into the second multi-tubular PFR unit to obtain a second saccharification liquid; and (c) supplying and saccharifying the second saccharification liquid into the PFR sets connected in series.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

Figure 1:
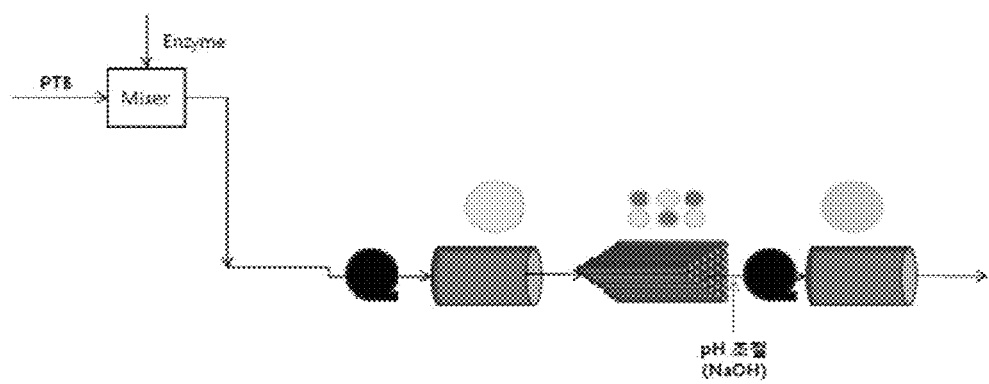
FIG. 1 is a schematic view showing a method for saccharifying biomass according to the present invention.
Figure 2:
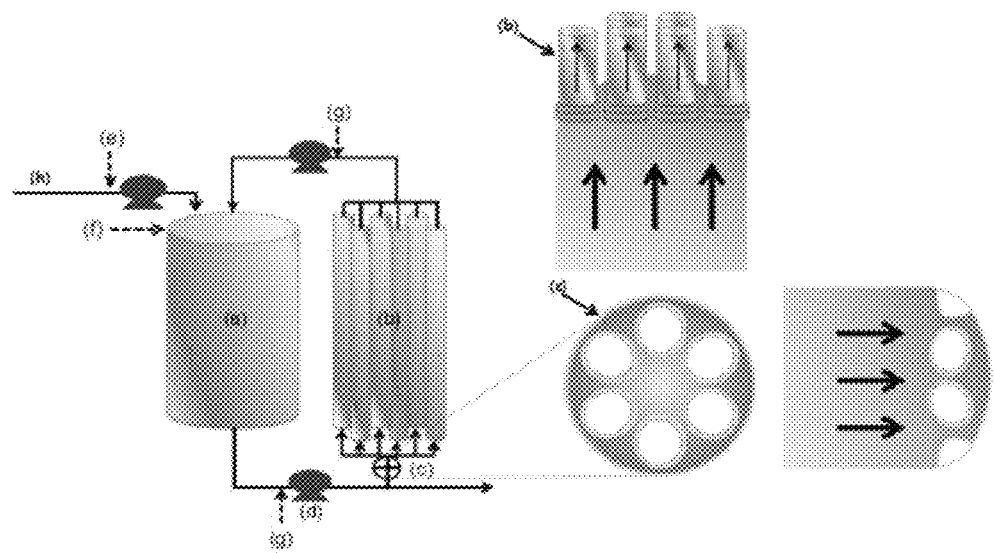
FIG. 2 shows a process of recycling a portion or all of biomass from a second multi-tubular PFR unit to a first single-tubular PFR unit according to an embodiment of the present invention and also shows a perforated plate disposed in the inlet of the second multi-tubular PFR unit.
Figure 3:
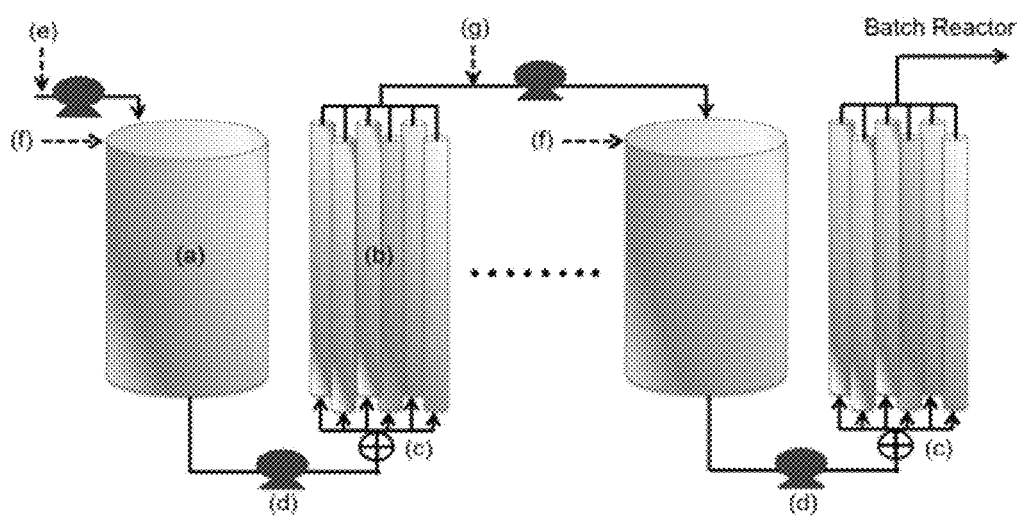
FIG. 3 shows a biomass saccharification apparatus comprising PFRs connected in series according to an embodiment of the present invention.

In the present invention, saccharification experiments were performed using two PFR units having different diameters (FIG. 1). Specifically, in a biomass saccharification experiment according to an embodiment (FIG. 2), a saccharification liquid produced was recycled to a first single-tubular PFR unit, and in a biomass saccharification experiment according to another embodiment (FIG. 3), passage of the saccharification liquid through a PFR set comprising a first single-tubular PFR unit and a second multi-tubular PFR unit was repeated several times. As a result, it was found that a high concentration of a sugar compound could be obtained without having to use an additional mixer.

In an embodiment of the present invention (FIG. 2), a saccharification experiment was performed by saccharifying pretreated biomass with a saccharifying enzyme in a first single-tubular PFR to obtain a first saccharification liquid, distributing the first saccharification liquid into a second multi-tubular PFR unit to obtain a second saccharification liquid, and recycling a portion or all of the second saccharification liquid to the first single-tubular PFR unit. As a result, it was found that a high concentration of a sugar compound can be obtained without having to use an additional mixer.

Therefore, in one aspect, the present invention is directed to a fractionated coupled apparatus for saccharifying biomass, comprising: (a) a first single-tubular plug-flow reactor (PFR) unit; (b) a second multi-tubular PFR unit comprising 2-100 PFRs, each having a diameter smaller than that of the first single-tubular PFR unit; and (c) a means for recycling a portion or all of a saccharification liquid obtained in the second multi-tubular PFR unit to the first single-tubular PFR unit.

In another aspect, the present invention is directed to a method for saccharifying biomass, comprising the steps of: (a) mixing pretreated biomass (PTB) with a saccharifying enzyme to obtain a mixture, and passing the mixture through a first single-tubular plug-flow reactor (PFR) unit to obtain a first saccharification liquid; (b) distributing the first saccharification liquid into a second multi-tubular PFR unit to obtain a second saccharification liquid; and (c) recycling a portion or all of the second saccharification liquid of step (b) to the first single-tubular PFR unit of step (a).

Biomass is mixed uniformly with enzyme and introduced into the first single-tubular PFR unit. The biomass stays in the first single-tubular PFR unit for a certain period of time to perform a first saccharification reaction. Because the saccharification reaction consumes oxygen, the efficiency of saccharification can be increased by supplying oxygen to the first single-tubular PFR unit, and introduction of external contaminants into the first single-tubular PFR unit can be prevented by positive pressure. The biomass that stayed for a certain period of time is transferred to a second multi-tubular PFR unit by a mono pump. Herein, because the second multi-tubular PFR unit comprises PFRs, each having a diameter smaller than that of the first single-tubular PFR unit, the biomass is distributed into the second multi-tubular PFR unit, and thus naturally mixed. According to this process, even biomass having a high solid content (20-30%) can be mixed by distribution without having to use an additional mixer or an additional viscosity control process. After completion of the second saccharification reaction, a portion or all of the second saccharification liquid is recycled to the first single-tubular PFR unit and continues to be saccharified. Herein, the saccharification liquid fractions that are recycled from the second multi-tubular PFR unit are combined and mixed in a tube while being transferred to the first single-tubular PFR unit.

In another embodiment (FIG. 3) of the present invention, pretreated biomass together with a saccharifying enzyme was supplied to and saccharified in a first single-tubular PFR unit to obtain a first saccharification liquid, and the first saccharification liquid was distributed into and further saccharified in a second multi-tubular PFR unit to obtain a second saccharification liquid. The second saccharification liquid was passed 2-10 times through a PFR set having the same structure as that of a combination of the first FPR unit and the second multi-tubular PFR unit. As a result, it was found that a high concentration of a sugar compound could be obtained without having to use an additional mixer.

In still another aspect, the present invention is directed to a fractionated coupled apparatus for saccharifying biomass, comprising 2-10 plug-flow reactor (PFR) sets connected in series, wherein each of the PFR sets comprises: (a) a first single-tubular plug-flow reactor (PFR) unit; and (b) a second multi-tubular PFR unit comprising 2-100 PFRs, each having a diameter smaller than that of the first single-tubular PFR unit.

In yet another aspect, the present invention us directed to a method for saccharifying biomass, comprising: (a) mixing pretreated biomass (PTB) with a saccharifying enzyme to obtain a mixture, and supplying and saccharifying the mixture to and in PFR sets, each comprising a first single-tubular plug-flow reactor (PFR) unit and a second multi-tubular PFR unit; (b) distributing a first saccharification liquid, produced in the first single-tubular PFR unit, into the second multi-tubular PFR unit to obtain a second saccharification liquid; and (c) supplying and saccharifying the second saccharification liquid to and in the PFR sets connected in series.

The processes ranging from supply of the biomass mixed with the enzyme to saccharification in the second multi-tubular PFR unit are as described above.

After completion of the second saccharification reaction, the second saccharification liquid is supplied to other PFR set having the same structure as that of the PFR set. The second saccharification liquid is supplied as a raw material to a PFR unit having the same structure as that of the first single-tubular PFR unit of other PFR set, and the other PFR unit performs a saccharification reaction using the saccharification liquid, after which the saccharification liquid produced in the other PFR unit is supplied to another PFR unit. This process may be repeated 1-10 times, thereby producing a final saccharification liquid. Herein, the saccharification liquid can be produced even when biomass is passed only once through the PFR set. However, it is preferred to pass biomass several times through the PFR set in order to increase the efficiency of saccharification. If biomass is passed more than 10 times through the PFR set, the efficiency of saccharification will increase, but the size of the saccharification plant will increase and the amount of energy used will increase, thus increasing costs. For this reason, it is preferred to pass biomass 10 times or less through the PFR set.

In the present invention, the pretreated biomass and the saccharifying enzyme may be mixed by passage through a refiner. Because the pretreated biomass contains a large amount of solid components, it is difficult to mix the pretreated biomass with the saccharifying enzyme by a general mixer. For this reason, the pretreated biomass containing a large amount of solids is preferably mixed with the saccharifying enzyme by use of a refiner. The refiner that is used in the present invention preferably has a suitable capacity selected depending on the amount and viscosity of the biomass, and the shape or material of the refiner is not limited, as long as the refiner can achieve suitable mixing.

In the present invention, saccharification in the first single-tubular PFR unit may be performed at a temperature of 50 to 75° C. Saccharification in the first single-tubular PFR unit is a process that is performed using a PFR having a relatively large diameter, and it may preferably be performed at a temperature of 50 to 75° C. If saccharification in the first single-tubular PFR unit is performed at a temperature lower than 50° C., the efficiency of the saccharification reaction will decrease, and if the saccharification temperature is higher than 75° C., the saccharifying enzyme will be inactivated.

In the present invention, saccharification in the second multi-tubular PFR unit may be performed at a temperature of 50 to 75° C. and a pH of 4-6. Saccharification in the second multi-tubular PFR unit is a process that is performed using PFRs having a diameter smaller than that of the first single-tubular PFR unit, and it may preferably be performed at a temperature of 50 to 75° C. If saccharification in the second multi-tubular PFR unit is performed at a temperature lower than 50° C., the efficiency of the saccharification reaction will decrease, and if the saccharification temperature is higher than 75° C., the saccharifying enzyme will be inactivated. In addition, the saccharification in the second multi-tubular PFR unit is performed at a pH lower than 4 or higher than 6, inactivation of the saccharifying enzyme will occur.

In the present invention, the diameter of each PFR in the second multi-tubular PFR unit may be 0.01-0.9 times the diameter of the first single-tubular PFR unit. The biomass subjected to the first saccharification process in the first single-tubular PFR unit is distributed into the second multi-tubular PFR unit and further saccharified therein. Preferably, the second multi-tubular PFR unit comprises 2-100 reactors, each having a diameter smaller than that of the first single-tubular PFR unit, and the diameter of each PFR in the second multi-tubular PFR unit is 0.01-0.9 times the diameter of the first single-tubular PFR unit. If the diameter of each PFR in the second multi-tubular PFR unit is less than 0.01 times the diameter of the first single-tubular PFR unit, the saccharification liquid will not smoothly flow through the second multi-tubular PFR unit, and if the diameter of each PFR in the second multi-tubular PFR unit is more than 0.9 times the diameter of the first single-tubular PFR unit, distribution of the saccharification liquid based on the difference in diameter between the PFRs will not be achieved, and thus the overall saccharification efficiency will decrease.

In the present invention, the diameter of the outlet of the first single-tubular PFR unit and/or the second multi-tubular PFR unit may be 0.5-1 times the diameter of the inlet thereof. If the diameter of the outlet of the PFR unit is smaller than the diameter of the inlet, the saccharification liquid in the PFR unit can be naturally mixed while it moves to the outlet of the PFR unit. However, if the ratio of the outlet diameter to the inlet diameter is less than 1:0.5, the diameter of the outlet will become too narrower to interfere with the flow of the saccharification liquid, and if the ratio of the outlet diameter to the inlet diameter is more than 1:1 so that the outlet diameter is larger, it will be difficult to achieve the mixing effect. In addition, where the PFRs having a smaller outlet diameter are used, the pressure in the outlet can increase to provide the effect of promoting saccharification.

In the present invention, the first single-tubular PFR unit performs a saccharification reaction using oxygen supplied thereto, and may further comprise a means for supplying oxygen. The saccharification reaction is generally a reaction in which the saccharifying enzyme uses oxygen to saccharify biomass. Particularly, in order to maximize the activity of the enzyme LPMO (lytic polysaccharide mono-oxygenases) acting on cellulosic saccharification, oxygen supply should be optimized. Thus, if oxygen is supplied to the reactor, the overall saccharification efficiency can be increased. In addition, because the inside of the reactor can be maintained at a pressure higher than that of the outside of the reactor due to oxygen that is applied to the reactor, abnormal reactions caused by external microorganisms can be minimized. In addition, biomass or the saccharification liquid is supplied to the top of the first single-tubular PFR unit, and for this reason, if oxygen is supplied to the top of the reactor, it will be supplied throughout the reactor by mixing. Thus, oxygen is preferably supplied to the top of the first single-tubular PFR unit, but is not limited thereto.

The apparatus according to the present invention may further comprise a mono pump for transferring the saccharification liquid to the first single-tubular PFR unit and/or the second multi-tubular PFR unit while increasing the efficiency of mixing of the saccharification liquid. Although the saccharification liquid can be transferred by gravity and pressure, the mono pump is preferably disposed at the first single-tubular PFR unit and/or the second multi-tubular PFR unit in order to transfer the saccharification liquid. Herein, the capacity of the pump is preferably selected in view of the effects of the internal pressure of the reactor and gravity, and a means for supplying an additive is preferably disposed in front of the pump so that the saccharification liquid and the additive will be naturally mixed with each other during transfer. The additive that is used in the present invention may be sodium hydroxide (NaOH) and/or a surfactant.

In the present invention, a perforated plate for distribution of the saccharification liquid may be disposed at the inlet of the second multi-tubular PFR unit. The perforated plate is a circular plate having a plurality of holes formed therein. To one side of the perforated plate, either the first single-tubular PFR unit consisting of a single PFR or a transfer tube is coupled. To the other side of the perforated plate, the second multi-tubular PFR unit consisting of a plurality of PFRs is coupled to a plurality of holes. The perforated plate functions to enable the saccharification liquid to be distributed uniformly in the second multi-tubular PFR unit consisting of a plurality of tubes. The perforated plate may be used without limitation as long as it has a shape enabling the saccharification liquid to be distributed uniformly in the second multi-tubular PFR unit.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Process for Producing 220,000 Ton/Year of Cellulosic Sugar

To analyze the economic efficiency of the biomass saccharification apparatus, a process capable of producing 220000 tons/year of cellulosic sugar was designed.

TABLE 1

Estimated throughput of biomass saccharification apparatus
Design Basis of Continuous Biomass Liquefying Reactor (CBLR)

| | | |
|---|---|---|
| Capacity (Ton Sugars/yr)-Estimated Yearly Production | 220,000 | Ton Sugars/yr |
| Capacity (BD Ton biomass/yr | 428,041 | BD Ton biomass/yr |
| Conversion yield (Ton sugars/BD Ton biomass) | 0.5140 | |
| Solid Consistency (%) | 25% | |
| Capacity (wet Ton PTB/yr) | 1,712,164 | Wet Ton PTB/yr |
| Operation day | 330 | Day |
| Capacity (wet Ton PTB/hr) | 216 | Wet Ton PTB/yr |
| EH reaction Time (hr) | 8 | Hr |
| Continuous Biomass Liquefying Reactor Volume (Ton) | 1,729 | Ton |

It was estimated that pretreated biomass having a solid content of 25% would be supplied in an amount of 216 wet ton/hr and would be sufficiently liquefied after 8 hours. In addition, the total reactor volume determined considering a reaction time of 8 hours was 1729 ton. Based on such considerations, processing elements could be designed as shown in Table 2 below.

The reactor height was assumed to be 16 m for a single-tubular PFR and 10 m for a multi-tubular PFR unit. The single-tubular PFR was assumed to have a diameter of 6.5 m, and the multi-tubular PFR unit was composed of six PFRs, each having a diameter of 0.64 m. It was shown that the pretreated biomass could be liquefied and saccharified through a total of three fractionated/coupled processes. Thus, it was shown that, when the single-tubular reactor and the multi-tubular reactor unit were continuously used three times, they could show efficiency similar to or higher than conventional biomass saccharification apparatuses, and that the overall size of the system used could be significantly reduced compared to those of conventional reactors.

In addition, it was shown that the saccharification apparatus of the present invention require reduced investment and power consumption compared to conventional biomass saccharification apparatuses comprising a stirrer.

It was shown that, in the case of the present invention in which stirring is performed only using relatively inexpensive pumps (several ten million won (Korean currency), investment can be reduced by up to 97% compared to the case of conventional biomass saccharification apparatuses that use expensive stirrers (several hundred million to several billion won). In addition, with respect to power consumption, it was shown that the saccharification apparatus of the present invention uses pumps that consume a power of about 40 kW (10 kW per each of four pumps), whereas conventional saccharification apparatuses that use stirrers require an increased amount of power (226-354 kW).

Thus, it was found that the saccharification apparatus of the present invention requires low investment and operational costs compared to conventional saccharification apparatuses and can show the same performance as that of conventional saccharification apparatuses.

INDUSTRIAL APPLICABILITY

As described above, according to the present invention, biomass is first saccharified in a PFR having a relatively

TABLE 2

Processing elements of biomass saccharification apparatus

| | Number of distributions | | | | | |
|---|---|---|---|---|---|---|
| | 1 | | 2 | | 3 | |
| Reactor Type | Single-tubular (coupled) | Multi-tubular (fractionated) | Single-tubular (coupled) | Multi-tubular (fractionated) | Single-tubular (coupled) | Multi-tubular (fractionated) |
| Height (m) | 16 | 10 | 16 | 10 | 16 | 10 |
| Diameter (m) | 6.5 | 0.64 | 6.5 | 0.64 | 6.5 | 0.64 |
| Reactor volume (m³) | 530.7 | 3.2 | 530.7 | 3.2 | 530.7 | 3.2 |
| Number of reactors | 1.0 | 6.0 | 1.0 | 6.0 | 1.0 | 6.0 |
| Density (Ton/m³) | 1.05 | 1.05 | 1.05 | 1.05 | 1.05 | 1.05 |
| Reactor volume (Ton) | 557.2 | 20.3 | 557.2 | 20.3 | 557.2 | 20.3 |
| Retention Time (hr) | 2.58 | 0.09 | 2.58 | 0.09 | 2.58 | 0.09 |
| Overall Time (hr) | 2.6 | 2.7 | 5.2 | 5.3 | 7.9 | 8.0 | large diameter, and then distributed into and saccharified in PFRs having a relatively small diameter. Thus, a high concentration of a sugar compound can be obtained without having to use an additional mixer.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of saccharifying biomass using a fractionated coupled apparatus for saccharifying biomass, comprising:
   (a) mixing pretreated biomass (PTB) with a saccharifying enzyme to obtain a mixture, and passing the mixture through a first single-tubular plug-flow reactor (PFR) unit to obtain a first saccharification liquid;
   (b) distributing the first saccharification liquid into a second multi-tubular PFR unit to obtain a second saccharification liquid, wherein the second multi-tubular PFR unit comprises 2-100 PFRs, each of the PFRs having a diameter smaller than that of the first single-tubular PFR unit; and
   (c) at least one of:
      (1) recycling a portion or all of the second saccharification liquid of the step (b) to the first single-tubular PFR unit of the step (a) using a means for recycling a portion or all of a saccharification liquid obtained in the second multi-tubular PFR unit, to the first single-tubular PFR unit;
      or
      (2) supplying and saccharifying the second saccharification liquid from step (b) into 2-10 PFR sets connected in series, wherein each of the PFR sets comprises:
         (a) a first single-tubular plug-flow reactor (PFR) unit; and
         (b) a second multi-tubular PFR unit including 2-100 PFRs, each having a diameter smaller than that of the first single-tubular PFR unit.

2. The method of claim 1, wherein the pretreated biomass and the saccharifying enzyme are mixed by passing through a refiner.

3. The method of claim 1, wherein saccharification in the first single-tubular PFR unit is performed at a temperature of 50 to 75° C.

4. The method of claim 3, wherein saccharification in the second multi-tubular PFR unit is performed at a temperature of 50 to 75° C. and a pH of 4-6.

5. The method of claim 3, wherein saccharification in the second multi-tubular PFR unit is performed at a temperature of 50 to 75° C. and a pH of 4-6.

6. The method of claim 1, wherein saccharification in the second multi-tubular PFR unit is performed at a temperature of 50 to 75° C. and a pH of 4-6.

7. The method of claim 1, wherein a diameter of each PFR in the second multi-tubular PFR unit is 0.01-0.9 times a diameter of the first single-tubular PFR unit.

8. The method of claim 7, wherein a diameter of an outlet of the first single-tubular PFR unit and/or the second multi-tubular PFR unit is 0.5-1 times a diameter of an inlet thereof.

9. The method of claim 7, wherein a diameter of an outlet of the first single-tubular PFR unit and/or the second multi-tubular PFR unit is 0.5-1 times a diameter of an inlet thereof.

10. The method of claim 1, wherein a diameter of the outlet of the first single-tubular PFR unit and/or the second multi-tubular PFR unit is 0.5-1 times a diameter of an inlet thereof.

11. The method of claim 1, wherein saccharification is performed while supplying oxygen to a top of the first single-tubular PFR unit.

12. The method of claim 1, wherein a mono pump is disposed at the first single-tubular PFR unit and/or the second multi-tubular PFR unit in order to transfer the saccharification liquid and increase a mixing efficiency of the saccharification liquid.

13. The method of claim 12, wherein an additive is supplied to a front end of the mono pump.

14. The method of claim 13, wherein the additive is a surfactant and/or sodium hydroxide (NaOH).

15. The method of claim 1, wherein a perforated plate for distributing saccharification liquid is disposed at an inlet of the second multi-tubular PFR unit.

16. The method of claim 1, wherein the first single-tubular PFR unit further comprises a means for supplying oxygen at an upper portion thereof.

17. The method of claim 1, wherein saccharification in the first single-tubular PFR unit of the PFR sets is performed at a temperature of 50 to 75° C.

18. The method of claim 1, wherein saccharification in the second multi-tubular PFR unit of the PFR sets is performed at a temperature of 50 to 75° C. and a pH of 4-6.

19. The method of claim 1, wherein a diameter of each PFR in the second multi-tubular PFR unit of the PFR sets is 0.01-0.9 times a diameter of the first single-tubular PFR unit.

20. The method of claim 1, wherein a diameter of the outlet of the first single-tubular PFR unit and/or the second multi-tubular PFR unit of the PFR sets is 0.5-1 times a diameter of an inlet thereof.

21. The method of claim 1, wherein saccharification is performed while supplying oxygen to a top of the first single-tubular PFR unit in the PFR sets.

22. The method of claim 1, wherein a mono pump is disposed at the first single-tubular PFR unit and/or the second multi-tubular PFR unit of the PFR sets in order to transfer the saccharification liquid and increase a mixing efficiency of the saccharification liquid.

23. The method of claim 22, wherein an additive is supplied to a front end of the mono pump.

24. The method of claim 23, wherein the additive is a surfactant and/or sodium hydroxide (NaOH).

25. The method of claim 1, wherein a perforated plate for distributing saccharification liquid is disposed at an inlet of the second multi-tubular PFR unit of the PFR sets.

26. The method of claim 1, wherein the first single-tubular PFR unit of the PFR sets further comprises a means for supplying oxygen at an upper portion thereof.

\* \* \* \* \*